United States Patent [19]

Gold et al.

[11] 4,293,963

[45] Oct. 13, 1981

[54] UNRESTRAINED ELBOW PROSTHESIS

[75] Inventors: Barry L. Gold; Richard C. Bolesky, both of Warsaw, Ind.

[73] Assignee: Zimmer USA, Inc., Warsaw, Ind.

[21] Appl. No.: 121,559

[22] Filed: Feb. 14, 1980

[51] Int. Cl.³ .............................................. A61F 1/03
[52] U.S. Cl. .................................... 3/1.91; 128/92 C
[58] Field of Search ................. 3/1.91, 1.911, 1.9; 128/92 C

[56] References Cited

U.S. PATENT DOCUMENTS

| | | | |
|---|---|---|---|
| Re. 29,757 | 9/1978 | Helfet | 3/1.91 |
| 3,547,115 | 12/1970 | Stevens | 128/92 C X |
| 3,816,854 | 6/1974 | Schlein | 3/1.91 |
| 3,868,730 | 3/1975 | Kaufer et al. | 128/92 C X |
| 3,879,766 | 4/1975 | Lowe et al. | 128/92 C X |
| 3,990,118 | 11/1976 | Strickland et al. | 3/1.91 |
| 4,008,495 | 2/1977 | Cavendish et al. | 3/1.91 |
| 4,038,704 | 8/1977 | Ring | 3/1.91 |
| 4,057,858 | 11/1977 | Helfet | 3/1.91 |
| 4,079,469 | 3/1978 | Wadsworth | 3/1.91 |
| 4,112,522 | 9/1978 | Dadurian et al. | 3/1.91 |
| 4,131,956 | 1/1979 | Treace | 3/1.91 |
| 4,193,139 | 3/1980 | Walker | 3/1.91 |

*Primary Examiner*—Clifford D. Crowder

*Attorney, Agent, or Firm*—Margaret L. Geringer; Richard H. Brink

[57] ABSTRACT

The prosthesis disclosed is an unrestrained or hingeless elbow prosthesis including a humeral implant component and an ulnar implant component. The metal humeral component is comprised of an elongated stem with a substantially cylindrical articulating surface on the distal end of said stem wherein said cylindrical articulating surface is convex such that the diameters of the end surfaces of the cylindrical shape are smaller than the diameter about the midportion of the cylindrical shape. The ulnar component is comprised of a metal retainer and a polyethylene bearing. The metal retainer includes an elongated stem attached to a metal base such that the stem depends from the base and anatomically curves slightly outward or laterally from the base.

The polyethylene bearing is slidably engaged to the metal retainer and locks into position on the retainer. The polyethylene bearing contains a concave cylindrical cavity for receiving the convex cylinder of the humeral component.

The metal humeral component then rotates about the axis of its cylindrical articulating surface within the cavity of the polyethylene ulnar bearing of the ulnar component.

4 Claims, 10 Drawing Figures

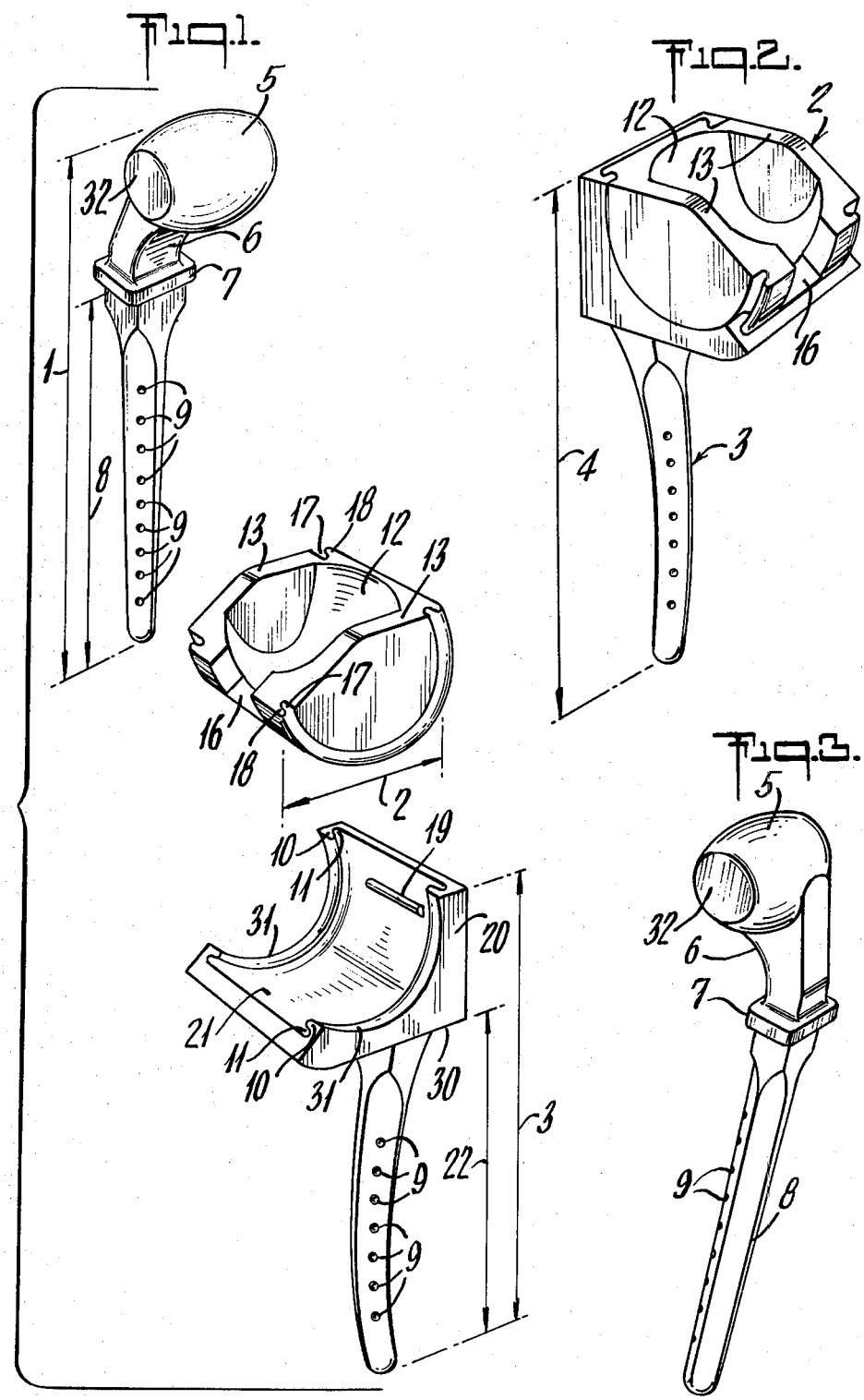

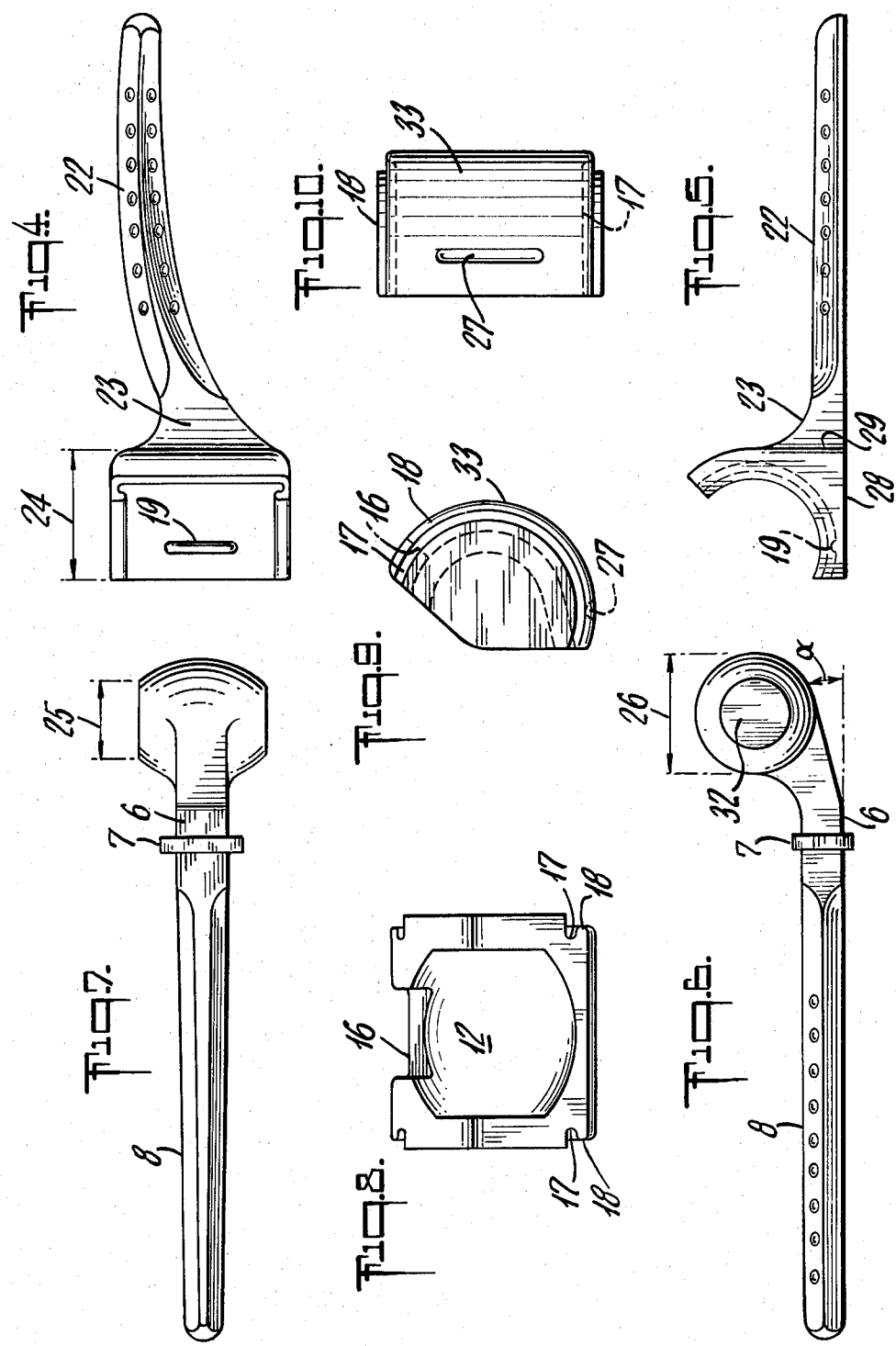

UNRESTRAINED ELBOW PROSTHESIS

BACKGROUND OF THE INVENTION

The invention generally relates to bone joint prostheses, and more particularly is concerned with an elbow prosthesis which allows a limited amount of medial-lateral motion in addition to flexion and extension motion. In addition, it presents a means of affixing a polyethylene bearing member to a metal ulnar component.

Elbow prostheses are generally totally restrained (hinged), semirestrained or unrestrained (hingeless).

In the past, many two component prostheses employed a metal on metal articulating surface. This results in abrasion of the contacting parts and release of metallic particles which are dispersed to the tissue surrounding the implant. This is an undesirable result. It has been found that a metal on non-metal articulating surface is much more desirable and provides better wear characteristics. Often one component is made of metal and one is made of a non-metal material such as polyethylene. In recent years, many prostheses utilize a metal component with a metal retained or reinforced polyethylene bearing surface. This allows a metal on polyethylene bearing surface, but still allows the strong support of the metal retainer.

U.S. Pat. No. 3,816,854 to Schlein discloses a hinged prosthesis for the elbow join including a humeral component terminating in a partial cylinder. A polyethylene bearing member is fitted within the partial cylinder and is provided with a slot. The ulnar component includes a U-shaped member having arms for supporting a pin. The pin engages the slot in the bearing member to provide rotation between the components.

U.S. Pat. No. 3,868,730 to Kaufer, et al. and U.S. Pat. No. 4,112,522 to Dadurian, et al. discloses other examples of joint prostheses which employ inserts between rotating member.

OBJECTS OF THE INVENTION

A principal object of the invention is to provide an unrestrained total elbow prosthesis which allows a limited amount of medial-lateral motion in addition to flexion and extension motion.

Another object of the invention is to provide an unrestrained total elbow having a means of firmly engaging a polyethylene bearing member to a metal retained ulnar prosthesis stem.

SUMMARY OF THE INVENTION

The present invention accomplishes all of the above objects of invention. The present invention provides an unrestrained elbow which allows a limited amount of medial-lateral motion in addition to flexion and extension motion. By providing a limited amount of medial-lateral motion, the chances of the prosthesis loosening is reduced. The medial-lateral motion is achieved due to the configuration of the articulating surface. The humeral articulating surface is substantially cylindrical with the barrel portion of the cylinder being convex as opposed to an axially straight sided cylinder. This convex cylindrical humeral surface mates with a concave cylindrical cavity having a concave articulating ulnar surface between two parallel side walls. The fit is loose enough to allow a limited amount of medial-lateral motion, but the side walls restrain excessive medial-lateral motion. Flexion and extension motion occurs about the axis of the convex cylindrical surface of the humeral component.

Each of the mating articulating surfaces are disposed on an end of an elongated stem for implantation into the corresponding medullary canal of the humerus and ulna.

The ulnar component consists of a bio-compatible metal retainer with a stem and a base and a slidably located bio-compatible polyethylene bearing locked onto the metal base at its proximal end. The polyethylene bearing contains the ulnar articulating surface.

The humeral component is formed of a bio-compatible metal. Thus, the articulating motion is of a metal humeral component on a polyethylene ulnar component which is metal retained.

DESCRIPTION OF THE DRAWINGS

These features and objects of the invention as well as others will become apparent to those skilled in the art by referring to the accompanying drawings in which:

FIG. 1 is an exploded perspective view illustrating the left assembly of the total unrestrained elbow prosthesis according to the invention, and further illustrating the relationship between the metal humeral component, the polyethylene ulnar bearing and the metal ulnar retainer as viewed from the top.

FIG. 2 is a perspective view of the assembled left ulnar component of the unrestrained elbow prosthesis as viewed from the top.

FIG. 3 is a perspective view of the humeral component of the unrestrained elbow prosthesis as viewed from the bottom.

FIG. 4 is a top plan view of the left metal ulnar retainer of the elbow prosthesis according to the invention.

FIG. 5 is a side elevational view of the left metal ulnar retainer of FIG. 4.

FIG. 6 is a side elevational view of the humeral component of the elbow prosthesis according to the invention.

FIG. 7 is a bottom view of the humeral component of FIG. 6.

FIG. 8 is a front end view of polyethylene ulnar bearing of the elbow prosthesis of this invention.

FIG. 9 is a side elevational view of the polyethylene ulnar bearing of FIG. 8.

FIG. 10 is a bottom view of the polyethylene ulnar bearing of FIG. 8.

DETAILED DESCRIPTION OF THE INVENTION

FIG. 1 illustrates the total unrestrained elbow prosthesis according to this invention. FIG. 1 shows a humeral component 1, an ulnar bearing 2 and an ulnar retainer 3. The humeral component 1 and the ulnar retainer 3 are formed of a bio-compatible metal. The ulnar bearing 2 is formed of a non-metal, such as polyethylene which is also bio-compatible. The polyethylene bearing 2 slidably locates and locks into the metal ulnar retainer 3 as shown in FIG. 2 to form an ulnar component 4 with a polyethylene articulating surface to mate with the metal articulating surface of the humeral component 1.

The metal humeral component 1, as shown in FIGS. 1, 3, 6 and 7, is comprised of an elongated stem 8, a supporting collar 7, a neck 6 and a humeral articulating surface 5. The elongated stem 8 is substantially diamond shaped in cross-section, and is longitudinally straight.

Since the stem 8 is straight, this allows the same humeral component to be used as both a left and right elbow prosthesis. As the collar 7, which outwardly extends from the stem 8, is approached, the stem 8 becomes more rectangular in cross-section. The collar 7 supports the humeral prosthesis 1 on the humeral bone when the elbow prosthesis is implanted. The elongated stem 8 is inserted into the reamed medullary canal in the standard manner used for stemmed prosthesis. Bone cement is used in the canal for more secure fixation. The collar 7 then supports the humeral component 1 on the bone surrounding the opening to the medullary canal so that the humeral prosthesis 1 is maintained in proper position. The supporting collar 7 limits the depth to which the humeral component 1 is inserted into the medullary canal. The articulating surface 5 is located at the distal end of the humeral component 1. A neck portion 6 separates the articulating surface 5 from the collar 7. The neck 6 angles upward from the straight longitudinal stem, as shown in FIG. 6 at approximately 15 degrees, indicated as $\alpha$. The articulating surface is substantially cylindrical in shape. The cylindrical shape is convex about the axis of the cylinder shape, such that the flat circular ends 32 of the cylinder shape have a smaller diameter 25 than the diameter of the mid-portion 26 of the cylindrical shape as shown in FIGS. 6 and 7.

The ulnar component 4 is comprised of a metal ulnar retainer 3, a polyethylene bearing 2 and an engaging means for attaching the bearing 2 to the retainer 3.

The metal retainer 3 of the ulnar component 4 is shown in FIGS. 1, 2, 4 and 5, and is comprised of an elongated stem 22 and a widened base support 23 and an enlarged base 24 on the proximal end of the stem 22. The elongated stem 22 of the metal retainer 3 has a slight curve to it which is convex laterally and follows the corresponding curve of the proximal part of the ulnar shaft. Because of this, separate metal retainers 3 have to be made for left and right elbows. FIG. 4 illustrates a top view of a left ulnar retainer and shows the convex curvature well. A right ulnar retainer would have a curvature opposite in direction to that shown in FIG. 4.

The elongated stem 22 is triangular in cross-section. The flat back side of the elongated triangular stem 22 widens into a base support 23 which further spreads into a first rectangular shaped flat plane 28 with a second substantially rectangular shaped plane 29 projecting upward at a 90 degree angle from the first rectangular plane 28 as shown in FIG 5, by lines 28 and 29 which project the rectangular planes. Each of said planes has some thickness so as to create a base with two parallel retaining walls 20 separated by a retaining platform 21 wherein each retaining wall 20 as well as the retaining platform 21 has an L-shaped outer configuration 30 and a C-shaped inner configuration 31 for supporting the polyethylene bearing surface which is attached by an engaging means to the metal base.

The polyethylene bearing is illustrated in FIGS. 1, 2, 8, 9 and 10 and has a cylindrical outer surface 33 for mating with the retaining platform 21 of the metal retainer 3, and an inner concave substantially cylindrical articulating surface 12 for mating with or receiving the said substantially convex articulating surface of the humeral component. Both of said inner and outer surfaces 12 and 33, respectively, are disposed between two parallel side walls 13. The bearing 2 contains a slot 16 which potentially allows for the humeral stem to fit upon full flexion of the elbow joint when in use.

Upon implantation, the elongated stem 22 of the ulnar component is placed in the medullary canal of the ulna. Again, bone cement is used to assist in stronger fixation. The second rectangular plane 29 functions in the same supporting manner as the collar 7 on the humeral component 1.

The ulnar component 4 includes an engaging means for securing the polyethylene bearing 2 to the metal retainer 3. The ulnar component 4 includes a first pair of circular ribs 10 and a first pair of circular grooves 11 on the metal base 24 of the ulnar retainer 3, with one circular rib 10 and one circular groove 11 being disposed on the inner side of each of said parallel retaining walls 20. The ulnar component 4 includes a second pair of circular ribs 18 and a second pair of circular grooves 17 on the polyethylene bearing 2, with one circular rib 18 and circular groove 17 being disposed on the outer surface of each of the bearing's parallel side walls 13.

The engaging means is adapted such that the first pair of circular grooves 11 slidably receives the second pair of circular ribs 18 and the second pair of circular grooves 17 slidably receives the first pair of circular ribs 10. Engagement of the non-metal bearing 2 into the metal retainer 3 is achieved by circular rotation of the bearing while the pairs of grooves and ribs are engaged.

The engaging means also includes a means of locking the bearing 2 onto the retainer 3. The locking means includes a longitudinal protuberance 19 located on the retaining platform 21, as shown in FIGS. 1, 4 and 5. The locking means further includes a longitudinal indentation 27 on the outer cylindrical surface 33 of the polyethylene bearing 2. As the polyethylene bearing 2 is being rotated onto the metal retainer 3 by engaging the pairs of grooves and ribs, further forced rotation allows the longitudinal protuberance 19 on the retaining platform 21 to engage the corresponding longitudinal indentation 27 on the outer cylindrical surface 33 of the bearing 2 to engage and subsequently lock the bearing 2 into place on the metal retainer 3. The clearance between the bearing 2 and the retaining platform 21 of the ulnar retainer 3 is so tight that much force is needed to cause this engagement and whereby, subsequent to the engagement of the longitudinal protuberance and corresponding longitudinal indentation, the non-metal bearing 2 is permanently locked onto the retainer 3 and there is no further motion between these two parts. This locking engagement is done by the prosthesis manufacturer and not by the surgeon.

It is commonly known that the use of some type of texture on prosthesis stems ensures a better fixation of bone cement to the prosthesis stem. The particular embodiment of the invention shown in FIGS. 1-6 illustrate the use of a plurality of semi-spherical indentations spaced along the length of the stem of both the humeral and ulnar components, 1 and 4, respectively.

The combination of the convex cylindrical articulating surface 5 of the humeral component 1 and the mating concave cylindrical articulating surface 12 of the ulnar bearing 2 located on the ulnar component 4, provides an unrestrained elbow which allows a limited amount of medial-lateral motion in addition to the normal flexion and extension motion. If the articulating surface employed an axially straight-sided cylinder surface, only the flexion and extension motion would be allowed. The concave cylindrical surface 12 of the bearing 2 is disposed between two parallel side walls 13.

The fit of the humeral articulating surface 5 into the cavity created by the ulnar articulating surface 12 and the side walls 13 is loose enough to allow a limited amount of medial-lateral motion which is desirable, but the side walls 13 restrain excessive medial-lateral motion. Flexion and extension motion occurs about the axis of the convex cylindrical surface of the humeral component.

The invention described here in an unrestrained elbow which allows a limited amount of medial-lateral motion in addition to flexion and extension motion. The invention also describes a means of engaging and securely locking a polyethylene ulnar bearing onto a metal ulnar retainer. While this invention has been described and exemplified in terms of its preferred embodiment, those skilled in the art can appreciate that modifications can be made without departing from the spirit and scope of this invention.

We claim:

1. An unrestrained elbow prosthesis comprised of the combination of:
   (a) a humeral component formed of a bio-compatible metal alloy having an elongated stem with a substantially cylindrical articulating surface on the distal end of said stem and a supporting collar outwardly extending from the stem and located toward the distal end of the stem, but proximal to the substantially cylindrical articulating surface and separated from the cylindrical surface by a neck portion, said substantially cylindrical surface being convex such that the diameter of the midportion of the cylindrical shape is greater than the flat circular ends of the cylindrical shape; and
   (b) an ulnar component consisting of a bio-compatible metal alloy retainer, and a bio-compatible non-metal bearing and an engaging means for attaching said non-metal bearing to the metal retainer and wherein the retainer has an elongated stem and an enlarged metal base portion attached to the proximal end of said elongated stem by a widened base support portion, said stem having a side which spreads into a first rectangular shaped flat plane with a second substantially rectangular plane projecting upward at a 90 degree angle from the first rectangular plane, each of said planes having some thickness so as to create said metal base portion with two parallel retaining walls separated by a retaining platform wherein each retaining wall, as well as the retaining platform, has an L-shaped outer configuration and a C-shaped inner configuration for supporting the non-metal bearing attached by the engaging means to the metal base, said non-metal bearing having a cylindrical outer bearing surface for mating with the C-shaped retaining platform, an inner concave substantially cylindrical articulating bearing surface, for mating with or receiving the said substantially convex articulating surface of the humeral component, and two parallel side walls between which both of said inner and outer bearing surfaces are disposed, and wherein the engaging means for attaching said non-metal bearing to the metal retainer of the ulnar component includes a first pair of circular ribs and a first pair of circular grooves on the metal base with one circular rib and one circular groove being disposed on the inner side of each of said parallel retaining walls, and wherein the retaining platform is cylindrical and contains a longitudinal protuberance and wherein the engaging means also includes a second pair of circular ribs and a second pair of circular grooves on the non-metal bearing with one circular rib and one circular groove being disposed on the outer surface of each of said parallel side walls, and wherein the outer cylindrical surface of the non-metal bearing contains a longitudinal indentation, and said engaging means is adapted such that the first pair of circular grooves slidably receives the second pair of circular ribs and the second pair of circular grooves slidably receives the first pair of circular ribs whereby engagement of the non-metal bearing into the metal retainer is achieved by circular rotation of the bearing while the pairs of grooves and ribs are engaged, and whereby further forced circular rotation allows the longitudinal protuberance on the metal retaining platform to engage the corresponding longitudinal indentation on the outer cylindrical surface of the non-metal bearing to engage and subsequently lock the bearing into place on the metal retainer.

2. The prosthesis of claim 1 wherein the non-metal material of the bearing is polyethylene.

3. An unrestrained elbow prosthesis as described in claim 1 wherein said non-metal bearing contain a slot which allows for the humeral stem to fit upon fill flexion of the elbow joint.

4. An ulnar component for an unrestrained elbow prosthesis comprising a biocompatible metal alloy retainer, and a biocompatible non-metal bearing and an engaging means for attaching said non-metal bearing to the metal retainer and wherein the retainer has an elongated stem and an enlarged metal base portion attached to the proximal end of said elongated stem by a widened base support portion, said stem having a side which spreads into a first rectangular shaped flat plane with a second substantially rectangular plane projecting upward at a 90 degree angle from the first rectangular plane, each of said planes having some thickness so as to create said metal base portion with two parallel retaining walls separated by a retaining platform wherein each retaining wall, as well as the retaining platform, has an L-shaped outer configuration and a C-shaped inner configuration for supporting the non-metal bearing attached by the engaging means to the metal base, said non-metal bearing having a cylindrical outer bearing surface for mating with the C-shaped retaining platform, an inner concave substantially cylindrical articulating bearing surface for receiving a mating articulating surface of a humeral component, and two parallel side walls between which both of said inner and outer bearing surfaces are disposed, and wherein the engaging means for attaching said non-metal bearing to the metal retainer of the ulnar component includes a first pair of circular ribs and a first pair of circular grooves on the metal base with one circular rib and one circular groove being disposed on the inner side of each of said parallel retaining walls, and wherein the retaining platform is cylindrical and contains a protuberance means and wherein the engaging means also includes a second pair of circular ribs and a second pair of circular grooves on the non-metal bearing with one circular rib and one circular groove being disposed on the outer surface of each of said parallel side walls, and wherein the outer cylindrical surface of the non-metal bearing contains an indentation means, and said engaging means is adapted such that the first pair of circular grooves slidably receives the second pair of circular ribs and the second pair of circular grooves slidably receives the first pair of circular ribs whereby engagement of the non-metal bearing into the metal retainer is achieved by circular rotation of the bearing while the pairs of grooves and ribs are engaged, and whereby further forced circular rotation allows the protuberance means on the metal retaining platform to engage the corresponding indentation means on the outer cylindrical surface of the non-metal bearing to engage and subsequently lock the bearing into place on the metal retainer.

* * * * *